US005510239A

United States Patent [19]

Baracchini, Jr. et al.

[11] Patent Number: 5,510,239
[45] Date of Patent: Apr. 23, 1996

[54] OLIGONUCLEOTIDE MODULATION OF MULTIDRUG RESISTANCE-ASSOCIATED PROTEIN

[75] Inventors: Edgardo Baracchini, Jr., San Diego; Clarence F. Bennett, Carlsbad, both of Calif.

[73] Assignee: Isis Pharmaceuticals, Inc., Carlsbad, Calif.

[21] Appl. No.: 136,811

[22] Filed: Oct. 18, 1993

[51] Int. Cl.$^6$ ............................ C12Q 1/68; C07H 21/04
[52] U.S. Cl. .................... 435/6; 536/23.1; 536/24.5; 514/44; 435/240.2; 935/34; 935/36
[58] Field of Search ................ 514/44; 536/23.1, 536/24.5; 935/34, 36; 435/6, 240.2

[56] References Cited

U.S. PATENT DOCUMENTS

| | | | |
|---|---|---|---|
| 4,806,463 | 2/1989 | Goodchild et al. | 435/5 |
| 5,004,810 | 4/1991 | Draper | 536/27 |
| 5,034,506 | 7/1991 | Summerton et al. | 528/391 |
| 5,087,617 | 2/1992 | Smith | 514/44 |
| 5,098,890 | 3/1992 | Gewirtz et al. | 514/44 |
| 5,135,917 | 8/1992 | Burch | 514/44 |
| 5,166,195 | 11/1992 | Ecker | 514/44 |
| 5,194,428 | 3/1993 | Agrawal et al. | 514/44 |

OTHER PUBLICATIONS

B. Fakler et al (1994) J Biol Chem 269:16181–94.
S P Cole et al (Mar. 29, 1993) Gen Bank Accession No. L05628.
Stull et al. (1995) Pharmaceutical Research 12: 465–483.
Wu–Pong (1994) Pharmaceutical Technology 18: 102–114.
Miller et al. (1994) Parasitology Today 10: 92–97.
Wagner (1994) Nature 372: 333–335.
S. P. C. Cole, et al., Overexpression of a Transporter Gene in a Multidrug–Resistant Human Lung Cancer Cell Line, *Science*, vol. 258, Dec. 4, 1992, 1650–54.
S. P. C. Cole, et al., Multidrug Resistance–Associated Protein: Sequence Correction, *Science*, vol. 260, May 14, 1993, 879.
Shelagh E. L. Mirski, et al., Multidrug Resistance in a Human Small Cell Lung Cancer Cell Line Selected in Adriamycin, *Cancer Research*, 47, 2594–2598, May 15, 1987.
Shelagh E. L. Mirski, et al., Antigens Associated with Multidrug Resistance in H69AR, a Small Cell Lung Cancer Cell Line, *Cancer Research*, 49, 5719–5724, Oct. 15, 1989.
P. E. Nielsen et al., Sequence–Selective Recognition of DNA by Strand Displacement with a Thymine–Substituted Polyamide, *Science*, vol. 254, 1497–1500.
M. L. Slovak, et al., Localization of a Novel Mutlidrug Resistance–Associated Gene in the HT1080/DR4 and H69AR Human Tumor Cell Lines, *Cancer Research*, 53:3221–225 Jul. 15, 1993.
A. R. Thierry, et al., Overcoming Multidrug Resistance in Human Tumor Cells Using Free and Liposomally Encapsulated Antisense Oligodeoxyucleotides, *Biochem.*
G. Vasanthakumar, et al., Modulation of Drug Resistance in a Daunorubicin Resistant Subline with Oligonucleoside Methylphosphonates, *Cancer Comm.*, vol. 1, No. 4, 1989, 225–232.

*Primary Examiner*—Jacqueline M. Stone
*Assistant Examiner*—Bruce R. Campell
*Attorney, Agent, or Firm*—Law Offices of Jane Massey Licata

[57] ABSTRACT

Compositions and methods are provided for the treatment and diagnosis of diseases or conditions amenable to treatment through modulation of the synthesis or metabolism of multidrug resistance-associated protein (MRP). In accordance with preferred embodiments, oligonucleotides are provided which are specifically hybridizable with nucleic acids encoding multidrug resistance-associated protein (MRP). Methods of treating animals suffering from diseases or conditions amenable to therapeutic intervention by modulating multidrug resistance with an oligonucleotides specifically hybridizable with RNA or DNA corresponding to multidrug resistance-associated protein (MRP) are disclosed. Methods of preventing the development of multidrug resistance and of improving the efficacy of chemotherapy are also-disclosed.

6 Claims, No Drawings

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
    ( A ) LENGTH: 20
    ( B ) TYPE: Nucleic Acid
    ( C ) STRANDEDNESS: Single
    ( D ) TOPOLOGY: Linear ( i v ) ANTI-SENSE: Yes ( x i ) SEQUENCE DESCRIPTION: SEQ ID NO: 1:

CGGGGCCGCA ACGCCGCCUG                                          20

( 2 ) INFORMATION FOR SEQ ID NO:2:

( i ) SEQUENCE CHARACTERISTICS:
    ( A ) LENGTH: 20
    ( B ) TYPE: Nucleic Acid
    ( C ) STRANDEDNESS: Single
    ( D ) TOPOLOGY: Linear ( i v ) ANTI-SENSE: Yes ( x i ) SEQUENCE DESCRIPTION: SEQ ID NO: 2:

CGGGGCCGCA ACGCCGCCTG                                          20

( 2 ) INFORMATION FOR SEQ ID NO:3:

( i ) SEQUENCE CHARACTERISTICS:
    ( A ) LENGTH: 20
    ( B ) TYPE: Nucleic Acid
    ( C ) STRANDEDNESS: Single
    ( D ) TOPOLOGY: Linear ( i v ) ANTI-SENSE: Yes ( x i ) SEQUENCE DESCRIPTION: SEQ ID NO: 3:

GGTGATCGGG CCCGGTTGCT                                          20

( 2 ) INFORMATION FOR SEQ ID NO: 4:

( i ) SEQUENCE CHARACTERISTICS:
    ( A ) LENGTH: 20
    ( B ) TYPE: Nucleic Acid
    ( C ) STRANDEDNESS: Single
    ( D ) TOPOLOGY: Linear ( i v ) ANTI-SENSE: Yes ( x i ) SEQUENCE DESCRIPTION: SEQ ID NO: 4:

CCGGTGGCGC GGGCGGCGGC                                          20

( 2 ) INFORMATION FOR SEQ ID NO: 5:

( i ) SEQUENCE CHARACTERISTICS:
    ( A ) LENGTH: 20
    ( B ) TYPE: Nucleic Acid
    ( C ) STRANDEDNESS: Single
    ( D ) TOPOLOGY: Linear ( i v ) ANTI-SENSE: Yes ( x i ) SEQUENCE DESCRIPTION: SEQ ID NO: 5:

AGCCCCGGAG CGCCATGCCG                                          20

( 2 ) INFORMATION FOR SEQ ID NO: 6:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 6:

TCGGAGCCAT CGGCGCTGCA        20

( 2 ) INFORMATION FOR SEQ ID NO: 7:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 7:

GGCACCCACA CGAGGACCGT        20

( 2 ) INFORMATION FOR SEQ ID NO: 8:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 8:

TGCTGTTCGT GCCCCGCCG        20

( 2 ) INFORMATION FOR SEQ ID NO: 9:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 9:

CGCGCTGCTT CTGGCCCCA        20

( 2 ) INFORMATION FOR SEQ ID NO: 10:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 10:

GCGGCGATGG GCGTGGCCAG        20

( 2 ) INFORMATION FOR SEQ ID NO: 11:

( i ) SEQUENCE CHARACTERISTICS:
        ( A ) LENGTH: 20

(B) TYPE: Nucleic Acid
(C) STRANDEDNESS: Single
(D) TOPOLOGY: Linear (iv) ANTI-SENSE: Yes (xi) SEQUENCE DESCRIPTION: SEQ ID NO: 11:

CAGGAGGTCC GATGGGGCGC                           20

(2) INFORMATION FOR SEQ ID NO: 12:

(i) SEQUENCE CHARACTERISTICS:
(A) LENGTH: 20
(B) TYPE: Nucleic Acid
(C) STRANDEDNESS: Single
(D) TOPOLOGY: Linear (iv) ANTI-SENSE: Yes (xi) SEQUENCE DESCRIPTION: SEQ ID NO: 12:

GCTCACACCA AGCCGGCGTC                           20

(2) INFORMATION FOR SEQ ID NO: 13:

(i) SEQUENCE CHARACTERISTICS:
(A) LENGTH: 20
(B) TYPE: Nucleic Acid
(C) STRANDEDNESS: Single
(D) TOPOLOGY: Linear (iv) ANTI-SENSE: Yes (xi) SEQUENCE DESCRIPTION: SEQ ID NO: 13:

AGGCCCTGCA GTTCTGACCA                           20

(2) INFORMATION FOR SEQ ID NO: 14:

(i) SEQUENCE CHARACTERISTICS:
(A) LENGTH: 20
(B) TYPE: Nucleic Acid
(C) STRANDEDNESS: Single
(D) TOPOLOGY: Linear (iv) ANTI-SENSE: Yes (xi) SEQUENCE DESCRIPTION: SEQ ID NO: 14:

CTCCTCCCTG GGCGCTGGCA                           20

(2) INFORMATION FOR SEQ ID NO: 15:

(i) SEQUENCE CHARACTERISTICS:
(A) LENGTH: 20
(B) TYPE: Nucleic Acid
(C) STRANDEDNESS: Single
(D) TOPOLOGY: Linear (iv) ANTI-SENSE: Yes (xi) SEQUENCE DESCRIPTION: SEQ ID NO: 15:

ACCGGATGGC GGTGGCTGCT                           20

(2) INFORMATION FOR SEQ ID NO: 16:

(i) SEQUENCE CHARACTERISTICS:
(A) LENGTH: 20
(B) TYPE: Nucleic Acid
(C) STRANDEDNESS: Single
(D) TOPOLOGY: Linear (iv) ANTI-SENSE: Yes ( x i ) SEQUENCE DESCRIPTION: SEQ ID NO: 16:

CGCATCTCTG TCTCTCCTGG    20

( 2 ) INFORMATION FOR SEQ ID NO: 17:

( i ) SEQUENCE CHARACTERISTICS:
  ( A ) LENGTH: 20
  ( B ) TYPE: Nucleic Acid
  ( C ) STRANDEDNESS: Single
  ( D ) TOPOLOGY: Linear ( i v ) ANTI-SENSE: Yes ( x i ) SEQUENCE DESCRIPTION: SEQ ID NO: 17:

CAGAAGCCCC GGAGCGCCAT    20

( 2 ) INFORMATION FOR SEQ ID NO: 18:

( i ) SEQUENCE CHARACTERISTICS:
  ( A ) LENGTH: 20
  ( B ) TYPE: Nucleic Acid
  ( C ) STRANDEDNESS: Single
  ( D ) TOPOLOGY: Linear ( i v ) ANTI-SENSE: Yes ( x i ) SEQUENCE DESCRIPTION: SEQ ID NO: 18:

GCCCCGCCG TCTTTGACAG    20

( 2 ) INFORMATION FOR SEQ ID NO: 19:

( i ) SEQUENCE CHARACTERISTICS:
  ( A ) LENGTH: 20
  ( B ) TYPE: Nucleic Acid
  ( C ) STRANDEDNESS: Single
  ( D ) TOPOLOGY: Linear ( i v ) ANTI-SENSE: Yes ( x i ) SEQUENCE DESCRIPTION: SEQ ID NO: 19:

GTGATGCTGT TCGTGCCCCC    20

( 2 ) INFORMATION FOR SEQ ID NO: 20:

( i ) SEQUENCE CHARACTERISTICS:
  ( A ) LENGTH: 20
  ( B ) TYPE: Nucleic Acid
  ( C ) STRANDEDNESS: Single
  ( D ) TOPOLOGY: Linear ( i v ) ANTI-SENSE: Yes ( x i ) SEQUENCE DESCRIPTION: SEQ ID NO: 20:

CTCACGGTGA TGCTGTTCGT    20

( 2 ) INFORMATION FOR SEQ ID NO: 21:

( i ) SEQUENCE CHARACTERISTICS:
  ( A ) LENGTH: 20
  ( B ) TYPE: Nucleic Acid
  ( C ) STRANDEDNESS: Single
  ( D ) TOPOLOGY: Linear ( i v ) ANTI-SENSE: Yes ( x i ) SEQUENCE DESCRIPTION: SEQ ID NO: 21:

CCCCCAGACA GGTTCACGCC    20

( 2 ) INFORMATION FOR SEQ ID NO: 22:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 22:

```
            CTGGCCCCCA GACAGGTTCA                                  20
```

( 2 ) INFORMATION FOR SEQ ID NO: 23:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 23:

```
            GCCAGGCTCA CGCGCTGCTT                                  20
```

( 2 ) INFORMATION FOR SEQ ID NO: 24:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 24:

```
            CACAGCCAGT TCCAGGCAGG                                  20
```

( 2 ) INFORMATION FOR SEQ ID NO: 25:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 25:

```
            CCTGGGTCTT CACAGCCAGT                                  20
```

OLIGONUCLEOTIDE MODULATION OF MULTIDRUG RESISTANCE-ASSOCIATED PROTEIN

FIELD OF THE INVENTION

This invention relates to diagnostics, research reagents and therapies for multidrug resistance and for disease states which respond to modulation of the phenomenon of multidrug resistance. In particular, this invention relates to antisense oligonucleotide interactions with certain messenger ribonucleic acids (mRNAs) or DNAs involved in the synthesis of the multidrug resistance-associated protein (MRP). Antisense oligonucleotides designed to hybridize to the mRNA encoding MRP are provided. These oligonucleotides have been found to lead to the modulation of the activity of the RNA or DNA, and thus to the modulation of the synthesis and metabolism of MRP. Palliation and therapeutic effect result.

BACKGROUND OF THE INVENTION

Acquired resistance to chemotherapy is a major problem in treatment of cancer by conventional cytotoxic drugs. Tumors may initially respond well to chemotherapy but later become resistant to a variety of unrelated drugs, leading to relapse. One cause of multidrug resistance is believed to be overexpression of a transmembrane transport protein known as P-glycoprotein or MDR protein. Another cause of multidrug resistance is believed to be overexpression of a member of the ATP-binding cassette transmembrane transporter superfamily known as multidrug resistance-associated protein (MRP). This protein is overexpressed in certain tumor cell lines which are multidrug resistant but do not overexpress P-glycoprotein. Cole et al. (1992) Science 258:1650–1654; Slovak et al., (1993) Cancer Res. 53:3221–3225.

Small-cell lung cancer accounts for 20–25% of all lung cancer. Up to 90% of small-cell lung cancers respond initially to chemotherapy, but nearly all become multidrug resistant, leading to relapse. The gene encoding MRP was initially isolated from a multidrug-resistant small-cell lung cancer cell line.

Agents capable of reversing the phenomenon of multidrug resistance and thus "sensitizing" the drug resistant tumors to chemotherapy are desired. Cyclosporin A and other agents are able to reverse doxorubicin resistance in cells which overexpress MDR, but clinical use of these compounds is limited by their cytotoxicity. Further, these reversing agents do not work in cells which overexpress MRP. Antisense oligonucleotides targeted to the MDR mRNA have been used to partially reverse the multidrug resistance phenotype. Thierry et al., (1993) Biochem. Biophys. Res. Comm. 190:952–960. Others have found that complete inhibition of P-glycoprotein (MDR protein) synthesis with antisense methylphosphonate oligonucleotides leads to only a partial decrease in drug resistance. Vasanthakumar, G. and N.K. Ahmed (1989) Cancer Commun. 1:225–232.

Interference with MRP expression is desired as a means for reversing the multidrug resistance phenomenon. Interference with MRP expression is also desired for improving the efficacy of conventional methods of cancer chemotherapy, particularly of lung cancer, most particularly of small-cell lung cancer.

OBJECTS OF THE INVENTION

It is a principal object of the invention to provide oligonucleotides and methods for modulating multidrug resistance through perturbation of the synthesis and expression of multidrug resistance-associated protein (MRP).

Reversing multidrug resistance using antisense oligonucleotides is an additional object of the invention, It is another object of the invention to provide oligonucleotides and methods for improving the efficacy of conventional methods of cancer chemotherapy.

It is a further object of the invention to provide antisense oligonucleotides which are capable of inhibiting the expression of multidrug resistance-associated protein (MRP).

Yet another object is to provide means for diagnosis of multidrug resistance.

These and other objects of this invention will become apparent from a review of the instant specification.

SUMMARY OF THE INVENTION

In accordance with the present invention, oligonucleotides are provided which specifically hybridize with nucleic acids encoding multidrug resistance-associated protein (MRP). The oligonucleotides are designed to bind either directly to mRNA or to a selected DNA portion forming a triple stranded structure, thereby modulating the amount of mRNA made from the gene. In either case, expression of MRP protein is ultimately modulated. "Hybridization," in the context of this invention, means hydrogen bonding, also known as Watson-Crick base pairing, between complementary bases, usually on opposite nucleic acid strands or two regions of a nucleic acid strand. Guanine and cytosine are examples of complementary bases which are known to form three hydrogen bonds between them. Adenine and thymine are examples of complementary bases which are known to form two hydrogen bonds between them. "Specifically hybridizable" indicates a sufficient degree of complementarity to avoid non-specific binding of the oligonucleotide to non-target sequences. It is understood that an oligonucleotide need not be 100% complementary to its target nucleic acid sequence to be specifically hybridizable.

The relationship between an oligonucleotide and its complementary target nucleic acid is commonly denoted as "antisense."

It is preferred to target specific genes for antisense attack. It has been discovered that the gene coding for MRP is particularly useful for this approach. Inhibition of MRP expression is expected to be useful for the treatment of multidrug resistance. However, "modulation" in the context of this invention means either an increase or decrease (stimulation or inhibition) of MRP expression.

Methods of modulating multidrug resistance comprising contacting an animal suspected of having multidrug-resistant tissues or cells with an oligonucleotide specifically hybridizable with nucleic acids encoding the MRP protein are provided. Methods for diagnosis are also a part of this invention.

DETAILED DESCRIPTION OF PREFERRED EMBODIMENTS

Oligonucleotides have recently become accepted as therapeutic moieties in the treatment of disease states in animals and man. For example, workers in the field have now identified antisense, triplex and other oligonucleotide therapeutic compositions which are capable of modulating expression of genes implicated in viral, fungal and metabolic diseases.

U.S. Pat. No. 5,098,890 is directed to antisense oligonucleotide therapies for certain cancerous conditions. U.S. Pat. No. 5,135,917 provides antisense oligonucleotides that inhibit human interleukin-1 receptor expression. U.S. Pat. No. 5,087,617 provides methods for treating cancer patients with antisense oligonucleotides. U.S. Pat. No. 5,166,195 provides oligonucleotide inhibitors of HIV. U.S. Pat. No. 5,004,810 provides oligomers capable of hybridizing to herpes simplex virus Vmw65 mRNA and inhibiting replication. U.S. Pat. No. 5,194,428 provides antisense oligonucleotides having antiviral activity against influenzavirus. U.S. Pat. No. 4,806,463 provides antisense oligonucleotides and methods using them to inhibit HTLV-III replication. Antisense oligonucleotides have been safely administered to humans and several clinical trials are presently underway. It is, thus, established that oligonucleotides can be useful therapeutic instrumentalities and that the same can be configured to be useful in treatment regimes for treatment of cells and animals, especially humans.

For therapeutics, an animal suspected of having a disease which can be treated by decreasing the expression of MRP is treated by administering oligonucleotides in accordance with this invention. Oligonucleotides may be formulated in a pharmaceutical composition, which may include carriers, thickeners, diluents, buffers, preservatives, surface active agents, liposomes or lipid formulations and the like in addition to the oligonucleotide. Pharmaceutical compositions may also include one or more active ingredients such as antimicrobial agents, antiinflammatory agents, anesthetics, and the like in addition to oligonucleotide. Oligonucleotides may be administered in conjunction with conventional cancer chemotherapeutic drugs which are well known to those skilled in the art.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable. Coated condoms or gloves may also be useful.

Compositions for oral administration include powders or granules, suspensions or solutions in water or non-aqueous media, capsules, sachets, or tablets. Thickeners, flavorings, diluents, emulsifiers, dispersing aids or binders may be desirable.

Formulations for parenteral administration may include sterile aqueous solutions which may also contain buffers, liposomes, diluents and other suitable additives.

Dosing is dependent on severity and responsiveness of the condition to be treated, but will normally be one or more doses per day, with course of treatment lasting from several days to several months or until a cure is effected or a diminution of disease state is achieved. Persons of ordinary skill can easily determine optimum dosages, dosing methodologies and repetition rates.

The present invention employs oligonucleotides for use in antisense inhibition of the function of RNA and DNA encoding multidrug resistance-associated protein (MRP). In the context of this invention, the term "oligonucleotide" refers to an oligomer or polymer of ribonucleic acid or deoxyribonucleic acid. This term includes oligomers consisting of naturally occurring bases, sugars and intersugar (backbone) linkages as well as oligomers having non-naturally occurring portions which function similarly. Such modified or substituted oligonucleotides are often preferred over native forms because of properties such as, for example, enhanced cellular uptake and increased stability in the presence of nucleases.

Specific examples of some preferred oligonucleotides envisioned for this invention may contain phosphorothioates, phosphotriesters, methyl phosphonates, short chain alkyl or cycloalkyl intersugar linkages or short chain heteroatomic or heterocyclic intersugar linkages. Most preferred are those with $CH_2$-NH-O-$CH_2$, $CH_2$-N($CH_3$)-O-$CH_2$, $CH_2$-O-N($CH_3$)-$CH_2$, $CH_2$-N($CH_3$)-N($CH_3$)-$CH_2$ and O-N($CH_3$)-$CH_2$-$CH_2$ backbones (where phosphodiester is O-P-O-$CH_2$). Also preferred are oligonucleotides having morpholino backbone structures. Summerton, J.E. and Weller, D.D., U.S. Pat. No. 5,034,506. In other preferred embodiments, such as the peptide-nucleic acid (PNA) backbone, the phosphodiester backbone of the oligonucleotide may be replaced with a polyamide backbone, the bases being bound directly or indirectly to the aza nitrogen atoms of the polyamide backbone. P.E. Nielsen, M. Egholm, R.H. Berg, O. Buchardt, Science 1991, 254, 1497. Other preferred oligonucleotides may contain sugar moieties comprising one of the following at the 2' position: OH, SH, $SCH_3$, F, OCN, $O(CH_2)_nNH_2$ or $O(CH_2)_nCH_3$ where n is from 1 to about 10; $C_1$ to $C_{10}$ lower alkyl, substituted lower alkyl, alkaryl or aralkyl; $C_1$; Br; CN; $CF_3$; $OCF_3$; O-, S-, or N-alkyl; O-, S-, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a conjugate; a reporter group; an intercalator; a group for improving the pharmacokinetic properties of an oligonucleotide; or a group for improving the pharmacodynamic properties of an oligonucleotide and other substituents having similar properties. Oligonucleotides may also have sugar mimetics such as cyclobutyls in place of the pentofuranosyl group. Base modifications or "universal" bases such as inosine may also be included.

The oligonucleotides in accordance with this invention preferably comprise from about 8 to about 30 nucleic acid base units. It is more preferred that such oligonucleotides comprise from about 15 to 25 nucleic acid base units. As will be appreciated, a nucleic acid base unit is a base-sugar combination suitably bound to an adjacent nucleic acid base unit through phosphodiester or other bonds.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed, however the actual synthesis of the oligonucleotides is well within the talents of the routineer. It is also known to use similar techniques to prepare other oligonucleotides such as the phosphorothioates and alkylated derivatives.

In accordance with this invention, persons of ordinary skill in the art will understand that messenger RNA identified by the open reading frames (ORFs) of the DNA from which they are transcribed includes not only the information from the ORFs of the DNA, but also associated ribonucleotides which form regions known to such persons as the 5'-untranslated region, the 3'-untranslated region, intervening sequence (intron) Thus, ribonucleotides and intron/exon junctions. oligonucleotides may be formulated in accordance with this invention which are targeted wholly or in part to these associated ribonucleotides as well as to the informational ribonucleotides. In preferred embodiments, the oligonucleotide is specifically hybridizable with a transcription initiation site, a translation initiation site, coding sequences and sequences in the 5'- and 3'-untranslated regions.

In accordance with this invention, the oligonucleotide is specifically hybridizable with portions of nucleic acids encoding multidrug resistance-associated protein (MRP). MRP belongs to the superfamily of ATP-binding cassette transport systems. This family includes the cystic fibrosis transmembrane conductance regulator, P-glycoprotein, and other transport proteins. The human MRP protein is 1531 amino acids in length and is encoded by an mRNA which is approximately 6.5 kb in length. Cole et al., (1992) Science 258:1650–1654; Cole et al., (1993) Science 260:879 (sequence correction); Slovak et al. (1993) Cancer Res. 53:3221–3225. Antisense oligonucleotides (shown in Table 1) were designed to be specifically hybridizable with sequences in the 5'-untranslated region, 3'-untranslated region and coding region of the MRP gene. Genbank accession number L05628; Cole et al., (1992) Science 258:1650–1654; Cole et al., (1993) Science 260:879 (sequence correction).

H69AR cells were treated with phosphorothioate oligonucleotides (SEQ ID NO: 1–16) in the presence of lipofectin, as described in the following examples. Oligonucleotides ISIS 7597 and ISIS 7598 (SEQ ID NO: 8 and SEQ ID NO: 9), both specifically hybridizable to the coding region of MRP, consistently inhibited steady-state MRP protein levels by greater than 30% compared to lipofectin controls in multiple ELISA experiments. In one experiment, ISIS 7597 inhibited MRP protein levels by over 95%. Oligonucleotides ISIS and 7598 are therefore preferred. It should be noted that the ELISA assay measures steady-state levels of MRP protein; because of the long half-life of the MRP protein, complete inhibition of MRP protein synthesis would be expected to be reflected as a decrease, but not complete loss, of MRP protein in these assays. This level of inhibition in this assay is considered to be significant. In Northern blot analysis of the effects of ISIS 7597 and 7598 on MRP mRNA levels, both oligonucleotides were demonstrated to virtually eliminate MRP mRNA expression.

Based on results obtained with the oligonucleotides of Table 1, additional phosphorothioate oligonucleotides were designed. These oligonucleotides are shown in Table 2.

TABLE 1

Antisense Oligonucleotides Specifically Hybridizable With MRP
(All are phosphorothioates; ISIS 7607 is also 2'0-me)

| ISIS # | TARGET REGION | SEQUENCE | SEQ ID NO: |
|---|---|---|---|
| 7607 | 5' UTR | CGG GGC CGC AAC GCC GCC UG | 1 |
| 7608 | 5' UTR | CGG GGC CGC AAC GCC GCC TG | 2 |
| 7606 | 5' UTR | GGT GAT CGG GCC CGG TTG CT | 3 |
| 7595 | 5' UTR | CCG GTG GCG CGG GCG GCG GC | 4 |
| 7592 | AUG | AGC CCC GGA GCG CCA TGC CG | 5 |
| 7593 | Coding | TCG GAG CCA TCG GCG CTG CA | 6 |
| 7594 | Coding | GGC ACC CAC ACG AGG ACC GT | 7 |
| 7597 | Coding | TGC TGT TCG TGC CCC CGC CG | 8 |
| 7598 | Coding | CGC GCT GCT TCT GGC CCC CA | 9 |
| 7599 | Coding | GCG GCG ATG GGC GTG GCC AG | 10 |
| 7600 | Coding | CAG GAG GTC CGA TGG GGC GC | 11 |
| 7601 | Coding | GCT CAC ACC AAG CCG GCG TC | 12 |
| 7603 | 3' UTR | AGG CCC TGC AGT TCT GAC CA | 13 |
| 7605 | 3' UTR | CTC CTC CCT GGG CGC TGG CA | 14 |
| 7602 | 3' UTR | ACC GGA TGG CGG TGG CTG CT | 15 |
| 7604 | 3' UTR | CGC ATC TCT GTC TCT CCT GG | 16 |

Preferred oligonucleotides useful in the invention comprise one of these sequences, or part thereof.

TABLE 2

Phosphorothioate Antisense Oligonucleotides
Specifically Hybridizable With MRP

| ISIS # | TARGET REGION | SEQUENCE | SEQ ID NO: |
|---|---|---|---|
| 8356 | AUG | CAG AAG CCC CGG AGC GCC AT | 17 |
| 8358 | Coding | GCC CCC GCC GTC TTT GAC AG | 18 |
| 8359 | Coding | GTG ATG CTG TTC GTG CCC CC | 19 |
| 8357 | Coding | CTC ACG GTG ATG CTG TTC GT | 20 |
| 8362 | Coding | CCC CCA GAC AGG TTC ACG CC | 21 |
| 8361 | Coding | CTG GCC CCC AGA CAG GTT CA | 22 |
| 8360 | Coding | GCC AGG CTC ACG CGC TGC TT | 23 |
| 8363 | 3' UTR | CAC AGC CAG TTC CAG GCA GG | 24 |
| 8364 | 3' UTR | CCT GGG TCT TCA CAG CCA GT | 25 |

Several preferred embodiments of this invention are exemplified in accordance with the following nonlimiting examples.

EXAMPLES

Example 1

Synthesis and characterization of oligonucleotides: Unmodified DNA oligonucleotides were synthesized on an automated DNA synthesizer (Applied Biosystems model 380B) using standard phosphoramidite chemistry with oxidation by iodine. β-cyanoethyldiisopropyl-phosphoramidites were purchased from Applied Biosystems (Foster City, CA). For phosphorothioate oligonucleotides, the standard oxidation bottle was replaced by a 0.2 M solution of 3H-1,2-benzodithiole-3-one 1,1-dioxide in acetonitrile for the stepwise thiation of the phosphite linkages. The thiation cycle wait step was increased to 68 seconds and was followed by the capping step.

2'-O-methyl phosphorothioate oligonucleotides were synthesized using 2'-O-methyl β-cyanoethyldiisopropyl-phosphoramidites (Chemgenes, Needham MA) and the standard cycle for unmodified oligonucleotides, except the wait step after pulse delivery of tetrazole and base was increased to 360 seconds. The 3'-base used to start the synthesis was a 2'-deoxyribonucleotide.

After cleavage from the controlled pore glass column (Applied Biosystems) and deblocking in concentrated ammonium hydroxide at 55° C. for 18 hours, the oligonucleotides were purified by precipitation twice out of 0.5 M NaCl with 2.5 volumes ethanol. Analytical gel electrophoresis was accomplished in 20% acrylamide, 8 M urea, 45 mM Tris-borate buffer, pH 7.0. Oligodeoxynucleotides and phosphorothioate oligonucleotides were judged from electrophoresis to be greater than 80% full length material.

The relative amounts of phosphorothioate and phosphodiester linkages obtained by this synthesis were periodically checked by $^{31}P$ NMR spectroscopy. The spectra were obtained at ambient temperature using deuterium oxide or dimethyl sulfoxide-$d_6$ as solvent. Phosphorothioate samples typically contained less than one percent of phosphodiester linkages.

Example 2

Selection and maintenance of multidrug resistant cell line H69AR cells: H69AR, a doxorubicin-resistant human small cell lung carcinoma cell line, was selected and maintained as described in Mirski et al. (1987) Cancer Res. 47:2594–2598.

Example 3

Lipofection and oligonucleotide treatment of H69AR cells for analysis by whole cell ELISA: $1.5 \times 10^6$ cells were plated into 35mm tissue culture wells and allowed to attach overnight. The cells were then washed twice with 3 ml of serum-free medium prior to lipofection. Oligonucleotides were added to a concentration of 0.3 μM in 1 ml of serum-free medium in a polystyrene tube. 10 μl of lipofectin (GIBCO/BRL) was then added and the mixture was vortexed. After ten minutes at room temperature the DNA/lipofectin suspension was added to the cells and incubated for four hours at 37° C. After this incubation 1 ml of 20% Hyclone serum in RPMI was added and left at 37° C. overnight. The next day the suspension was removed and replaced with fresh medium. On the following day the lipofection was repeated as before and the cells were harvested 8 hours after the second lipofection.

Example 4

Whole Cell ELISA of H69AR Cells after Oligonucleotide Treatment: Cells were harvested, counted and washed twice with PBS. Cells were resuspended at $0.5-1 \times 10^5$ cells/ml in PBS and 100 μl was plated in each well of an ELISA plate. Plates were dried overnight at 37° and autocrosslinked twice in a Stratalinker (Stratagene, La Jolla, CA). Plates were rehydrated in TBST, 200 μl/well for 2×5 minutes. Wells were blocked for 1.5–2 hours at room temperature with 200 μl TBST containing 5% NGS, 1% BSA. Primary antibody [50 μl of monoclonal antibody 3.186; Mirski et al. (1989) Cancer Res. 49:5719–5724] diluted in blocking solution was added and plates were incubated for 1.5–2 hours in a humidified chamber at room temperature. Plates were washed 3×5 minutes with 200 μl TBST. Plates were incubated with 50 μl secondary antibody diluted in blocking solution for 1–1.5 hours at room temperature in a humidified chamber. Plates were washed for with 200 μl TBST, 3×5 minutes. Color detection was by horseradish peroxidase [incubate with 100 μl OPD/$H_2O_2$/citrate buffer (250 μ mg/ml OPD in methanol/25μ3% $H_2O_2$/24.8 ml 0.05M citrate pH 5)] in the dark for 30 minutes at room temperature, stop reaction with 25 μl 8N $H_2SO_4$, and read absorbance at 490 nm] or by alkaline phosphatase [incubate with 50 μl substrate solution (1 PNPP tablet in 5 ml 50 mM $NaHCO_3$, pH 9.6, 1 mM $MgCl_2$) for 30 minutes in humid chamber at room temperature, stop reaction with 50 μl 0.4 M NaOH, read absorbance at 405 nm].

Example 5

RNA Analysis of H69AR Cells Treated with Antisense Oligonucleotides Specifically Hybridizable with MRP: $10 \times 10^6$ cells were plated per T75 flask and allowed to attach overnight. Cells were washed twice with serum-free medium before incubation with 6 ml of oligonucleotide/lipofectin suspension (0.3 μM oligonucleotide; 10 μl lipofectin per ml of serum-free medium) at 37° C. for 4 hours after which 6 ml of 20% Hyclone serum in RPMI was added and left overnight. Fresh medium was added the next day. On the following day polyadenylated RNA was isolated using a MICRO-FASTTRACK mRNA isolation kit (InVitrogen). The RNA was then separated by electrophoresis on a formaldehyde-agarose denaturing gel and then transferred to a nylon membrane (Zetaprobe, Biorad). The membrane was prehybridized in 50% formamide, 5x SSC, 5x Denhardt's solution, 1% SDS and 100 μg/ml sheared, denatured herring testis DNA for 4 hours at 42° C. The membrane was then hybridized overnight at 42° C. with a 2.0 kb cDNA fragment of MRP labelled with [α-$^{32}$P]dCTP using a random prime kit (GIBCO/BRL). The blot was washed three times in 0.1% SDS and 0.1x SSC for 20 minutes at 52° C. and autoradiographed. Only in overloaded lanes was any RNA detectable as a faint band after oligonucleotide treatment with ISIS 7597 and 7598.

What is claimed is:

1. An oligonucleotide selected from the group consisting of SEQ ID NO: 2, 3, 4, 5, 6, 7, 8, 9, 10, 11, 12, 13, 14, 15 and 16.

2. An oligonucleotide of claim 1 selected from the group consisting of SEQ ID NO: 8 and 9.

3. An oligonucleotide of claim 1 wherein at least one of the intersugar linkages between nucleotide units of the oligonucleotide is a phosphorothioate linkage.

4. A method of inhibiting the synthesis of multidrug resistance-associated protein in a cultured cell or tissue comprising contacting the cell or tissue with an isolated oligonucleotide selected from the group consisting of SEQ ID NO: 2, 3, 4, 5, 6, 7, 8, 9, 10, 11, 12, 13, 14, 15 and 16, so that synthesis of multidrug resistance associated protein is inhibited.

5. The method of claim 4 wherein the oligonucleotide is selected from the group consisting of SEQ ID NO: 8 and 9.

6. The method of claim 4 wherein at least one of the intersugar linkages between nucleotide units of the oligonucleotide is a phosphorothioate linkage.

* * * * *